(12) United States Patent
Sakaki

(10) Patent No.: US 9,072,803 B2
(45) Date of Patent: Jul. 7, 2015

(54) STERILIZATION DEVICE

(71) Applicant: PHARMABIO CORPORATION, Aichi (JP)

(72) Inventor: Akio Sakaki, Aichi (JP)

(73) Assignee: PHARMABIO CORPORATION, Aichi (JP)

( * ) Notice: Subject to any disclaimer, the term of this patent is extended or adjusted under 35 U.S.C. 154(b) by 0 days.

(21) Appl. No.: 14/160,960

(22) Filed: Jan. 22, 2014

(65) Prior Publication Data

US 2014/0205500 A1 Jul. 24, 2014

(30) Foreign Application Priority Data

Jan. 23, 2013 (JP) ................................. 2013-010556

(51) Int. Cl.
*A61L 9/00* (2006.01)
*A62C 13/62* (2006.01)
(Continued)

(52) U.S. Cl.
CPC . *A61L 2/18* (2013.01); *A61L 2/186* (2013.01); *A61L 2/22* (2013.01); *A61L 2202/11* (2013.01); *A61L 2202/14* (2013.01); *A61L 2202/25* (2013.01)

(58) Field of Classification Search
CPC ............... A61L 2/00; A61L 2/22; A61L 9/14; B05B 1/28
USPC ........ 239/302, 338; 422/1, 28, 105, 119, 123, 422/292, 306; 55/DIG. 46; 96/53, 200, 203, 96/319
See application file for complete search history.

(56) References Cited

U.S. PATENT DOCUMENTS 7,790,104 B2    9/2010   Adams et al.
2005/0175500 A1  8/2005   Adams et al.
(Continued)

FOREIGN PATENT DOCUMENTS

AU    2012100211    3/2012
JP    4426851       3/2010
(Continued)

OTHER PUBLICATIONS

Extended European Search Report, dated Apr. 10, 2014, in counterpart European Patent Application No. 14151577.5.

*Primary Examiner* — Monzer R Chorbaji
(74) *Attorney, Agent, or Firm* — Greenblum & Bernstein, P.L.C.

(57) ABSTRACT

To allow uniform and efficient sterilization of facilities selected from clean rooms, cell processing centers for human use (CPCs), medical-supply-manufacturing facilities, animal-rearing facilities (SPF animals), biohazard rooms, food processing facilities, and medical facilities, where walls, floors, ceilings, device surfaces, and spaces, including equipment interiors, can be sterilized while minimizing effects such as corrosion and using the smallest amount of chemical agent as possible, and whereby sterilization can be carried out without problems with residual toxicity and without the need for wiping operations subsequent to sterilization. In addition, an operator can initiate, monitor, and control sterilization from outside the sterilization zone and thus respond to unexpected circumstances such as damage to a sprayer during a sterilization operation. Moreover, a suitable sterilization environment can be produced and maintained automatically, and reliable sterilization can be carried out by a remote operator along with a main controller located at a distance that allows control.

15 Claims, 1 Drawing Sheet

(51) Int. Cl.
*A61M 11/06* (2006.01)
*B01D 19/00* (2006.01)
*A61L 2/18* (2006.01)
*A61L 2/22* (2006.01)

(56) References Cited

U.S. PATENT DOCUMENTS

2008/0247922 A1 10/2008 Adams et al.
2010/0201311 A1 8/2010 Lyell Kirby et al.
2011/0005261 A1* 1/2011 Lee et al. .................. 62/331
2011/0091354 A1 4/2011 Schwartz et al.
2012/0301356 A1 11/2012 Olson et al.
2013/0147428 A1 6/2013 Kirby et al.

FOREIGN PATENT DOCUMENTS

| WO | 03/082355 | 10/2003 |
| WO | 2010/093730 | 8/2010 |
| WO | 2011/047127 | 4/2011 |
| WO | 2012/173756 | 12/2012 |

* cited by examiner

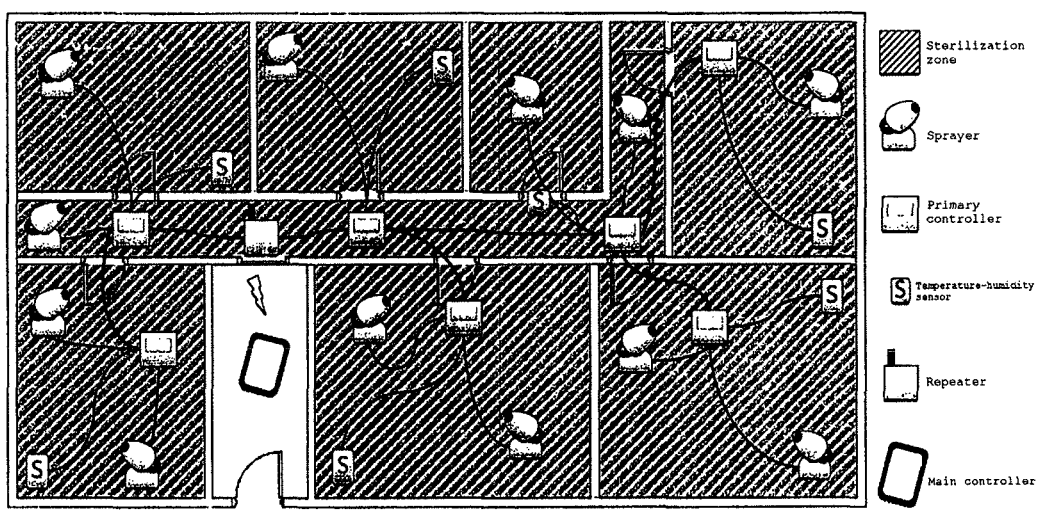

STERILIZATION DEVICE

TECHNICAL FIELD

The present invention relates to a device for sterilizing facilities that handle cells or animals, and more specifically relates to a device for sterilizing such facilities or the like by atomizing peracetic acid disinfectant with a sprayer, as well as a sterilization method that uses this device.

The present application asserts a priority claim for Japanese Patent Application 2013-010556, filed on Jan. 23, 2013, and the entire content thereof is incorporated by reference in the present specification.

BACKGROUND ART

It is necessary to periodically sterilize facilities in which microorganisms must be contained and facilities in which a degree of cleanliness must be maintained, such as clean rooms, cell processing centers for human use (CPCs), medical supplies manufacturing facilities, animal-rearing facilities (SPF animals), and biohazard rooms.

In the past, sterilization of these types of facilities has generally involved formalin fumigation, hypochlorite spraying, or glutaral application. However, the glutaral and formaldehyde that are used as disinfectants are carcinogenic, and there have been problems with residual toxicity due to their escape during wiping.

In addition, with regard to disinfection carried out by the application of chemical agent, considerable time is required for repeated application and wiping away of disinfectant after cleaning ceilings, walls, and floors. Moreover, with formalin fumigation, which has traditionally been used for sterilizing spaces, curing for preventing corrosion in installed equipment is required, and decontamination of surfaces and internal parts of installed equipment is not possible. In addition, since decontamination requires long periods of time (24 to 28 h), and a neutralization operation is also required, considerable time is needed.

Additionally, when disinfection is carried out by the application and wiping of chemical agents, although walls and floors can be disinfected, free-floating microorganisms within a space or microorganisms that are present inside or on the rear surfaces of devices that cannot be reached by hand cannot be disinfected. The effect of sterilization has thus been limited.

Consequently, no device has allowed efficient and uniform sterilization without problems with residual toxicity for a wide range of facilities such as clean rooms, cell processing centers for human use (CPCs), medical-supply-manufacturing facilities, animal-rearing facilities (SPF animals), and biohazard rooms

SUMMARY OF THE INVENTION

Problems to be Solved by the Invention

An object of the present invention is to provide a device allowing facilities such as clean rooms, cell processing centers for human use (CPCs), medical-supply-manufacturing facilities, animal-rearing facilities (SPF animals), biohazard rooms, food processing facilities, and medical facilities to be sterilized without problems with residual toxicity; and allowing walls, floors, ceilings, equipment surfaces, and spaces, including the interior of devices, to be uniformly and efficiently sterilized using as little chemical agent as possible while minimizing corrosive effects.

Means for Solving the Problems

In light of the problems with the prior art described above, the inventors of the present invention carried out painstaking investigations and discovered that by atomizing a peracetic acid disinfectant through adjusting the air level and chemical agent feed rate in a sprayer, droplets with extremely small diameter (dry fog) can be generated. In addition, when these droplets are sprayed in a facility such as a clean room or CPC, the droplets will not wet surfaces, thereby allowing sterilization to effectively occur without corrosive harm to installed equipment and the like in the facility.

Additionally, it was discovered that by using a repeater to control the communication of a main controller with a plurality of spraying units that are provided with sprayers, sterilization can be efficiently carried out by spraying chemical agent once uniformly over an entire facility having a plurality of rooms in a complicated arrangement. The present invention was thereby perfected.

Specifically, the present invention is:

(1) a sterilization device, comprising:
a plurality of sprayer units having:
one or more sprayers for atomizing peracetic acid disinfectant using forced air, and discharging droplets,
one or more temperature-humidity sensors, and
a primary controller;
a repeater; and
a main controller.

(2) The sterilization device according to (1), wherein the one or more sprayers and a temperature-humidity sensor are electrically connected to the primary controller.

(3) The sterilization device according to (1) or (2), wherein a primary controller having a plurality of sprayer units has a function that allows wired communication with the repeater, directly or via one or more of the primary controllers.

(4) The disinfecting device according to any of (1) to (3), wherein the main controller has a function that allows wireless communication with a repeater.

(5) The sterilization device according to any of (1) to (4), wherein the peracetic acid disinfectant is a mixture of peracetic acid, hydrogen peroxide, acetic acid, and water.

(6) A method for sterilizing a facility selected from a clean room, CPC (cell processing center for human use), medical supplies manufacturing facility, animal-rearing facility (SPF animals), biohazard room, food processing facility, or medical care facility, using the device according to any of (1) to (5).

Effects of the Invention

With the sterilization device of the present invention, installed devices and the like in a facility can be effectively sterilized without corrosion damage, because droplets of extremely small diameter can be discharged by atomizing the peracetic acid disinfectant with a sprayer. Nor is it necessary to carry out a liquid wiping operation, because the droplets will not wet the interior of the facility.

In addition, because peracetic acid has a wide antimicrobial spectrum, microorganisms such as sporulating bacteria that have not been killed by traditional technologies can be effectively sterilized using the sterilization device of the present invention.

Additionally, because a plurality of fumigator units provided with fumigators and primary controllers communicate under control of an repeater in the sterilization device of the present invention, chemical agent can be sprayed one time uniformly over an entire facility having a plurality of rooms in a complicated arrangement, thereby allowing efficient sterilization.

BRIEF DESCRIPTION OF THE DRAWINGS

FIG. 1 is a schematic view of the sterilization device according to an embodiment of the present invention.

DESCRIPTION OF THE PREFERRED EMBODIMENTS

In an embodiment of the present invention, the invention is a sterilization device provided with: a plurality of sprayer units having one or more sprayers for atomizing peracetic acid disinfectant using forced air, thereby discharging droplets, one or more temperature-humidity sensors, and a primary controller; a repeater; and a main controller. Specifically, the sterilization device of the present invention has a primary configuration comprising a plurality of sprayer units, repeaters, and main controllers.

The sprayers that are used in the present invention have no restrictions in regard to type or model, provided that they can reliably generate dry fog through the atomization of liquid using air.

The sprayers pertaining to the present invention are connected to controllers, and are made to operate or stand by under control of the controllers. One or more stages of forced air fans (e.g., two stages) may be present, making it possible to spray droplets out to 7 to 12 m. A turntable may also be used, thereby allowing spraying over a broad area. Moreover, the air that is used for spraying may be treated with a high-performance filter in order to remove 99.997% or more of particles of size 5 μm or greater.

An example of a fumigator that can be used as the fumigator in the present invention is an electric fumigator (Vectra-Jet 7505) manufactured by Fogmaster.

The repeater in the present invention preferably has a temperature-humidity logging function, where detected values for the temperature and humidity at the sprayer units are automatically recorded every minute. The log record can be stored in *.CSV format as a single file for each sterilization operation. The main controller can wirelessly check and record the repeater log.

The peracetic acid disinfectant that is used in the present invention preferably is a mixed liquid composed of peracetic acid, hydrogen peroxide, acetic acid, and water.

The preferred peracetic acid content of the peracetic acid disinfectant of the present invention is 0.01 to 1.2 wt %, the preferred hydrogen peroxide content is 0.06 to 4.8 wt %, and the preferred acetic acid content is 0.02 to 6.0 wt %, with the remainder being water. In addition, the peracetic acid disinfectant decomposes to oxygen, water, and acetic acid after sterilization. The acetic acid evaporates at room temperature and does not leave a residue.

Examples of peracetic acid disinfectants that can be used in the present invention include Actril© and Minncare© manufactured by Minntech, as well as other acetic acid-based chemical agents.

In the present invention, droplets of extremely small (micron-size) particle diameters can be reliably generated by adjusting the feed rate of air and chemical agent by regionally varying the supply voltages and frequencies of the sprayers described above. The center diameter of the droplets is preferably 3 to 15 μm, with 3 to 10 μm being additionally preferred. Extremely small droplets of this type are referred to as "dry fog" and have the characteristic of fog whereby wetting does not occur. Consequently, effective sterilization can be carried out without corroding installed equipment in a facility. In addition, because the interior of the facility is not wetted by the droplets, there is no need for operations involving wiping up liquid.

Because peracetic acid has a wide antimicrobial spectrum, high-level sterilization effects can be manifested whereby even sporulating bacteria and the like can be killed in a short period of time using the device of the present invention.

Temperature-humidity sensors are provided in the sprayer units of the present invention. The temperature-humidity sensors are connected to the primary controllers described below, and detected values for the measured temperature and humidity are transmitted to the primary controllers. The transmitted detection values are then displayed in real time on the primary controllers, and recording is carried out automatically at one minute intervals at the repeater. The recordings (logs) are recorded as *.CSV files in the repeater memory and can be checked and recorded by the main controller. In addition, in the present invention, the temperature-humidity sensors can be disposed at suitable locations in the facility at the time of sterilization.

Primary controllers are provided in the sprayer units in the present invention. The primary controllers in the present invention are electrically connected to the sprayers and the temperature-humidity sensors. The primary controllers initiate operation of the sprayers and carry out the sterilization treatment. During performance of the sterilization treatment, the primary controllers cause the ultrasonic atomizers to operate and stand by based on the detected values of the temperature-humidity sensors, so that the humidity levels that are detected by the temperature-humidity sensors are maintained at a preset humidity.

The preset humidity and humidity maintenance time can be manually inputted by the primary controllers in the present invention, and the primary controllers can be used in two modes, a stand-alone mode whereby they can carry out a sterilization treatment, and a network mode whereby they operate via a repeater.

Additionally, the primary controllers of the plurality of sprayer units in the present invention have a function that allows wired communication with the repeater.

The repeaters have a function that allows wireless communication with the main controller. The primary controllers thus have a function that allows communication in this manner and thereby have a function whereby automatic synchronizing of sterilization end times is possible (sterilization link function). The repeaters can monitor and record the temperature and humidity, passage of time, and remaining sterilization time for all of the primary controllers and can transmit these values to the main controller. In addition, all of the primary controllers or individual primary controllers can be controlled by indication of the primary controllers. The repeaters also maintain a sterilization link function during times when the main controller cannot communicate, thereby having a function that allows the sterilization end times of all of the spraying units to be synchronized.

Specifically, sterilization normally ends under direction of the sprayer units which have previously reached a set humidity, and the amount of generated fog from the sterilization device as a whole is thus decreased. By using the sterilization link function, the sterilization end times can be matched to the farthest primary controller, thereby ensuring there are no areas where sterilization will not occur.

For example, when a given room in a facility is narrow, and the humidity rises first relative to other locations, humidity suitable for sterilization is maintained at which condensation will not occur based on the measured humidity data from the temperature-humidity sensor that is connected to the primary controller. Thus, the humidity is maintained in order according to sprayer units that have reached a humidity suitable for sterilization. The sterilization times for the other sprayer units are thus automatically extended up until the sterilization end time of the sprayer unit that has finally reached the appropriate humidity, and premature termination and a decrease in humidity can thereby be prevented.

The sprayer unit of the present invention may also have a configuration in which a temperature-humidity sensor and one or more sprayers are provided along with a primary controller.

A main controller is provided in the sterilization device of the present invention. The main controller in the present invention can be placed outside the sterilization zone and can be used by an operator. The main controller has a function that allows wireless communication with a repeater that is placed in the sterilization zone. The repeater has a function for communicating with each of the primary controllers. The communication function may be achieved wirelessly or using wires. As a result of this communication function, the main controller can manage and monitor the status of the respective sprayer units (e.g., temperature, humidity, time passed, remaining sterilization time, sterilization link time), thereby making it possible to check sterilization conditions from outside the sterilization zone during the sterilization operation.

In addition, it is possible to operate (start, pause, stop) as well as change the settings (set humidity, sterilization time, sterilization link option) for all of the sprayer units or individual sprayer units. As a result, measures can be taken in light of unexpected circumstances such as damage to a sprayer during a sterilization operation.

The sterilization device of the present invention has a repeater that is electrically connected with some or all of the primary controllers, and the repeater can communicate wirelessly with the main controller. The repeater transmits data from each of the primary controllers to the main controller and also allows commands from the main controller to be transmitted to each of the primary controllers.

FIG. 1 is a schematic diagram showing a sterilization device and use thereof in the sterilization of the interior of a facility in accordance with an embodiment of the present invention.

The sterilization device of the present invention is suitable for use in the sterilization of facilities such as clean rooms, cell processing centers for human use (CPCs), medical-supply-manufacturing facilities, animal-rearing facilities (SPF animals), P2 and P3 biohazard rooms, food processing facilities, and medical facilities. In addition, the sterilization device of the present invention does not generate heat, as with formalin fumigation, so there is no difference in room pressure due to heating within the sterilization zone and outside the sterilization zone. Safety with respect to humans is also high, and the device can be used in a wide range of facilities, provided that air-tightness is improved by turning off the air conditioning, sealing up the facility, and the like.

With the sterilization device of the present invention, a maximum of ten repeaters can be used simultaneously with a single main controller. In addition, the respective repeaters can control a maximum of twenty sprayer units, and up to two sprayers may be attached to each sprayer unit. Specifically, a maximum of 400 sprayers can be controlled by a single main controller. A single sprayer can sterilize a space of up to about 100 m$^3$. In addition, the number of connections between the repeaters and the sprayer units can be increased as necessary.

By increasing the number of sprayer units in this manner, the sterilization device of the present invention can reliably carry out sterilization regardless of the size of the sterilization zone by controlling and maintaining suitable sterilization conditions for rooms, corridor ceilings, walls, floors, installed device surfaces and interiors, as well as spaces, provided that the air conditioning can be turned off and the sterilization zone can be sealed off readily by sealing doors and the like.

EXAMPLES

Example 1

A sterilization test was carried out using the sterilization device of the present invention. The details are described below.

Test facility: CPC (cell processing center; one room+ gowning+degowning areas; roughly 16 m$^2$ (38.4 m$^3$).

Sterilization device: Double fog system, manufactured by Pharma Bio (stand-alone prototype of the sterilizer of the present invention).

Disinfectant: 4% diluted solution of peracetic acid-based sterilization agent Minncure©, manufactured by Minntech.

Spraying conditions: The chemical agent was sprayed in the target facility and a humidity of 90% or greater was maintained for 3 hours.

After the sterilization test was carried out under the conditions described above, an evaluation was carried out based on sterilization validation, adhered microorganism assay, and free-floating microorganism assay. The evaluation methods are described below.

(1) Sterilization Validation

Bacteria indicator (BI): Filter paper-type biological indicator manufactured by Raven; 10$^6$ spores of the thermophile *G. stearothermophilus* (ATCC #7953).

Method: The material was placed in the sprayed space during peracetic acid spraying. After completion of the sterilization test, a determination was made by culturing for 24 h at 60° C. in SCDB (liquid medium).

(2) Adherent Bacteria Assay

Method: An assay was made after pressing the adherent bacterial media onto the assay surface for two seconds. Bacteria were cultured for 5 days at 32.5° C., and yeast were cultured for 5 days at 22.5° C., whereupon the colony numbers were determined.

Media used: Petan Check SCDL medium (bacteria) and CPPD medium (yeast) manufactured by Eiken Chemical Co., Ltd.

(3) Free-Floating Bacteria Assay

Method: An air sampler manufactured by Sysmex was used, and assays were carried out by directing a prescribed amount of air onto media for various cleanliness grades. Bacteria were cultured for 5 days at 32.5° C., and yeast were cultured for 5 days at 22.5° C., whereupon the colony numbers were determined.

Media: SCDL medium (bacteria, CPPD medium (yeast), manufactured by Kohjin Bio.

The results of sterilization validation are shown below.

TABLE 1

| No. | Installation location | Results |
| --- | --- | --- |
| BI1 | Degowning unit, wall surface | Negative (−) |

TABLE 1-continued

| No. | Installation location | Results |
|---|---|---|
| BI2 | Supply unit, wall surface | Negative (−) |
| BI3 | Cell preparation room, wall surface | Negative (−) |
| BI4 | Secondary gowning unit, wall surface | Negative (−) |
| BI5 | Supply unit floor surface | Negative (−) |
| BI6 | Secondary gowning unit, floor surface | Negative (−) |
| BI7 | Degowning unit, floor surface | Positive (+) |
| BI8 | Cell preparation room, floor surface, near entrance | Negative (−) |
| BI9 | Cell preparation room floor surface, below pass box | Negative (−) |
| BI10 | Frozen chemical storage, (door open)* positive control | Positive (+) |
| BI11 | Pass box 1, (door open) | Negative (−) |
| BI12 | Pass box 2, (door open) | Negative (−) |
| BI13 | $CO_2$ upper stage, upper middle (door open)* positive control | Positive (+) |
| BI14 | $CO_2$ upper stage, lower front (door closed)* positive control | Positive (+) |
| BI15 | $CO_2$ lower stage, upper middle (door open) | Negative (−) |
| BI16 | $CO_2$ lower stage, lower front (door open) | Negative (−) |
| BI17 | Safety cabinet, middle | Negative (−) |
| BI18 | Frozen chemical storage, Upper level, middle | Negative (−) |
| BI19 | Frozen chemical storage, lower stage, middle | Negative (−) |
| BI20 | Centrifuge, on rotor | Negative (−) |
| BI21 | Pass box 3 (door open) | Negative (−) |
| BI22 | Not used (positive control) | Positive (+) |
| BI23 | Media only (negative control) | Negative (−) |

As shown in Table 1, wall and floor surfaces of a CPC facility can be effectively sterilized using the sterilization device of the present invention. In addition, by simply opening the doors inside facilities during spraying, $10^6$ spores of BI that had been placed in equipment such as $CO_2$ incubators, safety cabinets, freezers, pass boxes, and the like can be killed.

The results of free-floating bacterial assays and adherent bacterial assays are presented in Table 2 below.

TABLE II

| No. | Assay location | Grade | Bacteria | Yeast | Determination | No. | Assay location | Grade | Bacteria | Yeast | Determination |
|---|---|---|---|---|---|---|---|---|---|---|---|
| Free floating bacteria 1 | Safety cabinet, inside | A | 0 | 0 | Pass | Adherent bacteria 37 | $CO_2$ lower rack, inside | B | 0 | 0 | Pass |
| Free-floating bacteria 2 | Cell preparation room, back | B | 0 | 0 | Pass | Adherent bacteria 38 | Pass box 2, inside | B | 0 | 0 | Pass |
| Free-floating bacteria 3 | Cell preparation room, near entrance | B | 0 | 0 | Pass | Adherent bacteria 39 | Pass box 3, inside | B | 0 | 0 | Pass |
| Free-floating bacteria 4 | Secondary gowning unit | B | 0 | 0 | Pass | Adherent bacteria 17 | Supply unit, front floor surface | C | 0 | 0 | Pass |
| Free-floating bacteria 5 | Supply unit | C | 0 | 0 | Pass | Adherent bacteria 18 | Degowning unit, floor surface | C | 1 | 0 | Pass |
| Free-floating bacteria 6 | Degowning unit | C | 0 | 0 | Pass | Adherent bacteria 19 | Secondary gowning unit, doorknob | B | 0 | 0 | Pass |
| Adherent bacteria 7 | Cell preparation room, wall surface 1 | B | 0 | 0 | Pass | Adherent bacteria 20 | Secondary gowning unit, doorknob | B | 0 | 0 | Pass |
| Adherent bacteria 8 | Cell preparation room, wall surface 2 | B | 0 | 0 | Pass | Adherent bacteria 21 | Cell preparation room, doorknob | B | 0 | 0 | Pass |

TABLE II-continued

| No. | Assay location | Grade | Bacteria | Yeast | Determination | No. | Assay location | Grade | Bacteria | Yeast | Determination |
|---|---|---|---|---|---|---|---|---|---|---|---|
| Adherent bacteria 9 | Secondary gowning unit, wall surface | B | 0 | 0 | Pass | Adherent bacteria 22 | Cell preparation room, doorknob | B | 0 | 0 | Pass |
| Adherent bacteria 10 | Supply unit, wall surface | C | 0 | 0 | Pass | Adherent bacteria 23 | Centrifuge, surface | B | 0 | 0 | Pass |
| Adherent bacteria 11 | Degowning unit, wall surface | C | 0 | 0 | Pass | Adherent bacteria 24 | Frozen chemical storage, surface | B | 0 | 0 | Pass |
| Adherent bacteria 12 | Cell preparation room, back, floor surface | B | 0 | 0 | Pass | Adherent bacteria 25 | Operations room, surface | B | 0 | 0 | Pass |
| Adherent bacteria 13 | Cell preparation room, center, floor surface | B | 0 | 0 | Pass | Adherent bacteria 26 | Pass box 1, surface | B | 0 | 0 | Pass |
| Adherent bacteria 14 | Cell preparation room, entrance, floor surface | B | 0 | 0 | Pass | Adherent bacteria 27 | Safety cabinet, surface | B | 0 | 0 | Pass |
| Adherent bacteria 15 | Secondary gowning unit, floor surface | B | 0 | 0 | Pass | Adherent bacteria 28 | $CO_2$ incubator, surface | B | 0 | 0 | Pass |
| Adherent bacteria 16 | Supply unit, back, floor surface | C | 0 | 0 | Pass | Adherent bacteria 29 | Pass box 2, surface | B | 0 | 0 | Pass |
| Adherent bacteria 33 | Frozen chemical storage, inside, upper rack | B | 0 | 0 | Pass | Adherent bacteria 30 | Secondary gowning unit, shelf surface | C | 0 | 0 | Pass |
| Adherent bacteria 34 | Pass box 1 inside | B | 0 | 0 | Pass | Adherent bacteria 31 | Supply unit freezer, surface | C | 0 | 0 | Pass |
| Adherent bacteria 35 | Safety cabinet, inside | A | 0 | 0 | Pass | Adherent bacteria 32 | Supply unit, shelf surface | C | 0 | 0 | Pass |
| Adherent bacteria 36 | $CO_2$ upper rack, inside | B | 0 | 0 | Pass | Adherent bacteria 40 | Supply unit freezer, inside | C | 0 | 0 | Pass |

As is clear from Table 2, good effects are obtained at all assay locations with regard to free-floating bacterial assays and adherent bacterial assays using the sterilization device of the present invention.

The invention claimed is:

1. A sterilization device, comprising:
 a plurality of sprayer assemblies having:
  one or more sprayers for atomizing peracetic acid disinfectant using forced air, and discharging droplets,
  one or more temperature-humidity sensors, and
  a primary controller;
 a repeater; and
 a main controller.

2. The sterilization device according to claim 1, wherein the one or more sprayers and the one or more temperature-humidity sensors are electrically connected to the primary controller.

3. The sterilization device according to claim 1, wherein the primary controller having the plurality of sprayer assemblies is configured to allow wired communication with the repeater, directly or via one or more of the primary controllers.

4. The sterilization device according to claim 1, wherein the main controller is configured to allow wireless communication with the repeater.

5. The sterilization device according to claim 1, wherein the peracetic acid disinfectant is a mixture of peracetic acid, hydrogen peroxide, acetic acid, and water.

6. A method for sterilizing a facility selected from a clean room, cell processing center for human use, medical supplies manufacturing facility, animal-rearing facility configured for specific pathogen-free animals, biohazard room, food processing facility, or medical care facility, using the device according to claim 1.

7. The sterilization device according to claim 1, wherein the droplets comprise a dry fog.

8. The sterilization device according to claim 1, wherein the droplets have a center diameter within a range of 3 μm to 15 μm.

9. The sterilization device according to claim 8, wherein the droplets have a center diameter within a range of 3 μm to 10 μm.

10. The sterilization device according to claim 1, wherein the atomizing comprises ultrasonic atomizing.

11. The sterilization device according to claim 1, wherein each of the one or more sprayers generates dry fog through atomization of liquid.

12. A sterilization device, comprising:
a plurality of sprayer assemblies having:
   one or more sprayers for ultrasonically atomizing a disinfectant, having a wide antimicrobial spectrum, using forced air, and discharging a dry fog,
   one or more temperature-humidity sensors, and
   a primary controller configured to control a spraying operation by the one or more sprayers in accordance with values detected by the one or more temperature-humidity sensors, so that humidly levels detected by the one or more temperature-humidity sensors are maintained at a preset humidity;
a repeater configured for communication with the primary controller; and
a main controller configured to manage and monitor a status of the plurality of sprayer assemblies in order that sterilization conditions may be checked from outside of an area to be sterilized.

13. The sterilization device according to claim 12, wherein the status includes temperature, humidity, an elapsed time, a remaining sterilization time, and a sterilization link time.

14. The sterilization device according to claim 13, wherein the sterilization link time is associated with a synchronization of sterilization end times for the plurality of sprayer assemblies.

15. The sterilization device according to claim 12, wherein the disinfectant comprises peracetic acid.

* * * * *